US008424923B2

(12) United States Patent
Inman, Jr. et al.

(10) Patent No.: US 8,424,923 B2
(45) Date of Patent: Apr. 23, 2013

(54) FLUID TRANSFER ASSEMBLY

(75) Inventors: William D. Inman, Jr., Saginaw, MI (US); Donald A. Jahn, Midland, MI (US); Robert L. Kain, Freeland, MI (US); Thomas C. Kreucher, Midland, MI (US); Jeffrey Paul Sage, Midland, MI (US); Blondine Van Roy, Wezembeek-Oppem (BE)

(73) Assignee: Dow Corning Corporation, Midland, MI (US)

( * ) Notice: Subject to any disclaimer, the term of this patent is extended or adjusted under 35 U.S.C. 154(b) by 998 days.

(21) Appl. No.: 12/090,815

(22) PCT Filed: Oct. 23, 2006

(86) PCT No.: PCT/US2006/041573
§ 371 (c)(1),
(2), (4) Date: Apr. 18, 2008

(87) PCT Pub. No.: WO2007/048072
PCT Pub. Date: Apr. 26, 2007

(65) Prior Publication Data
US 2008/0277926 A1    Nov. 13, 2008

Related U.S. Application Data

(60) Provisional application No. 60/729,427, filed on Oct. 21, 2005.

(51) Int. Cl.
*F16L 13/00* (2006.01)
(52) U.S. Cl.
USPC ................................ 285/285.1; 285/125.1

(58) Field of Classification Search ............ 285/133.11, 285/133.21, 133.3, 133.4, 133.5, 133.6, 125.1, 285/285.1, 286.1, 286.2, 293.1, 423, 332
See application file for complete search history.

(56) References Cited

U.S. PATENT DOCUMENTS

| | | | | |
|---|---|---|---|---|
| 2,032,576 A | * | 3/1936 | Hering | 285/286.1 |
| 2,735,699 A | * | 2/1956 | Chadbourne | 285/148.22 |
| 2,896,976 A | * | 7/1959 | Wiltse | 285/230 |
| 2,986,411 A | * | 5/1961 | Anderson | 285/293.1 |

(Continued)

FOREIGN PATENT DOCUMENTS

| | | |
|---|---|---|
| DE | 8608998 | 7/1986 |
| DE | 20004312 U1 | 8/2000 |
| EP | 0 738 852 A1 | 10/1996 |

OTHER PUBLICATIONS

Wei et al., "The Effect of Silicon Resit on the Heat Resistance Property of Silicon Rubber" and English Abstract., J. Polym. Sci., (7), 1969, 3 pages.

(Continued)

*Primary Examiner* — Aaron Dunwoody
(74) *Attorney, Agent, or Firm* — Howard & Howard Attorneys PLLC

(57) ABSTRACT

A fluid transfer assembly for transporting medicinal substances. The fluid transfer assembly includes flexible tubes and a manifold each comprising silicone. The manifold has an inner protrusion and connector portions having inner walls. Free ends of the tubes are inserted into complementary configured inner walls of the connector portions until each of the free ends abut the inner protrusion, which creates a continuous uninterrupted passageway between the inner bores of the tubes through the manifold.

27 Claims, 9 Drawing Sheets

U.S. PATENT DOCUMENTS

| | | | | |
|---|---|---|---|---|
| 3,035,958 | A * | 5/1962 | Wilkins | 156/294 |
| 3,402,731 | A * | 9/1968 | Martin | 137/375 |
| 3,463,691 | A * | 8/1969 | Martin | 156/294 |
| 3,473,833 | A * | 10/1969 | Bremer | 285/285.1 |
| 3,898,988 | A * | 8/1975 | Morgan | 604/86 |
| 3,904,228 | A * | 9/1975 | Maroschak | 285/133.11 |
| 4,109,944 | A * | 8/1978 | Curtin | 285/373 |
| 4,447,237 | A | 5/1984 | Frisch et al. | |
| 4,641,860 | A | 2/1987 | McMickle et al. | |
| 4,661,110 | A | 4/1987 | Fortier et al. | |
| 4,893,841 | A * | 1/1990 | Bowen | 285/15 |
| 4,927,183 | A * | 5/1990 | Steinmetz et al. | 285/21.2 |
| 4,931,116 | A * | 6/1990 | Rosenzweig | 156/85 |
| 4,997,213 | A * | 3/1991 | Traner et al. | 285/131.1 |
| 5,033,775 | A * | 7/1991 | Matte et al. | 285/133.11 |
| 5,248,171 | A * | 9/1993 | Briet | 285/133.3 |
| 5,335,944 | A * | 8/1994 | Mitsui et al. | 285/133.3 |
| 5,411,300 | A * | 5/1995 | Mitsui | 285/294.1 |
| 5,447,341 | A | 9/1995 | Hartel et al. | |
| 5,462,314 | A * | 10/1995 | Goto et al. | 285/21.2 |
| 6,152,186 | A | 11/2000 | Arney et al. | |
| 6,220,634 | B1 * | 4/2001 | Burrowes | 285/133.11 |
| 6,290,265 | B1 * | 9/2001 | Warburton-Pitt et al. | 285/131.1 |
| 6,308,992 | B1 | 10/2001 | Mitsui et al. | |
| 6,432,345 | B1 * | 8/2002 | Warburton-Pitt | 264/263 |
| 6,497,836 | B2 * | 12/2002 | Krause et al. | 264/263 |
| 6,540,261 | B1 * | 4/2003 | Schiavone et al. | 285/133.11 |
| 6,585,298 | B2 * | 7/2003 | Pålsson | 285/294.2 |
| 7,093,859 | B2 * | 8/2006 | Warburton-Pitt et al. | 285/131.1 |
| 7,488,008 | B2 * | 2/2009 | Hawkins | 285/332 |
| 7,708,923 | B1 * | 5/2010 | Helicke et al. | 264/261 |
| 2002/0047265 | A1 * | 4/2002 | Karhu et al. | 285/125.1 |
| 2002/0050663 | A1 | 5/2002 | Warburton-Pitt et al. | |
| 2004/0006709 | A1 | 1/2004 | Chen | |
| 2004/0067099 | A1 | 4/2004 | Warburton-Pitt | |
| 2004/0100093 | A1 * | 5/2004 | Leigh-Monstevens | 285/222 |
| 2004/0164453 | A1 | 8/2004 | Warburton-Pitt | |
| 2004/0164555 | A1 | 8/2004 | Warburton-Pitt et al. | |
| 2005/0104370 | A1 * | 5/2005 | Kim et al. | 285/133.11 |
| 2009/0243284 | A1 * | 10/2009 | Klingel et al. | 285/125.1 |

OTHER PUBLICATIONS

Complaint, *Saint-Gobain Performance Plastics Corporation*, Plaintiff, v. *Dow Corning Corporation, et al.*, Defendants; Civil Action No. 07-CV-40302-FDS, Nov. 27, 2007, 5 pages.

Notice of Dismissal Without Prejudice of Defendant Dow Corning Corporation, *Saint-Gobain Performance Plastics Corporation*, Plaintiff, v. *Dow Corning Corporation, et al.*, Defendants; Civil Action No. 07-CV-40302-FDS, Feb. 12, 2008, 2 pages.

Complaint, *W.L. Gore & Associates, Inc*, Plaintiff, v. *Saint-Gobain Performance Plastics Corporation*, Civil Action No. L08-CV-054, Jan. 7, 2008, 24 pages.

Civil Docket for Case #:1:08-cv-00054-BEL, U.S. District Court, District of Maryland (Baltimore), 7 pages.

Sani-tech—"STHT Silicone Tubing Systems" brochure, 46 pages.

"Beware of Unauthorized BioSimplex(TM) Manifold Copies", J & J Scientific Products, Inc. Pending Legal Notice, <http://www.jandjsp.com/pdf_documents/JJ_Patent_Pending_Legal_Notice.pdf> (dated Aug. 15, 2006; accessed Dec. 22, 2008), 1 page.

"Bio-Simplex(TM) Manifold Systems", J & J Scientific Products, Inc. Products, <http://www.jandjsp.com/bio_simplex_manifolds> (accessed Dec. 22, 2008); pp. 1-2.

"Saint-Gobain Acquires Plastic Manufacturer", J & J Scientific Products, Inc. News, <http://www.jandjsp.com/news> (dated Feb. 8, 2008; accessed Dec. 22, 2008); pp. 1-2.

Ex-Parte Reexamination Certificate for Reexamination Request No. 90/006,855, Nov. 12, 2003, 2 pages.

PCT/US2006/041573 PCT International Search Report, Aug. 6, 2007, 7 pages.

English language abstract for DE20004312, extracted from www.Delphion.com, Dec, 23, 2008.

European Search Report, Application No. EP 11 17 3988, Sep. 26, 2011, 7 pages.

International Search Report, Application No. PCT/US2006/041573, Aug. 6, 2007, 7 pages.

\* cited by examiner

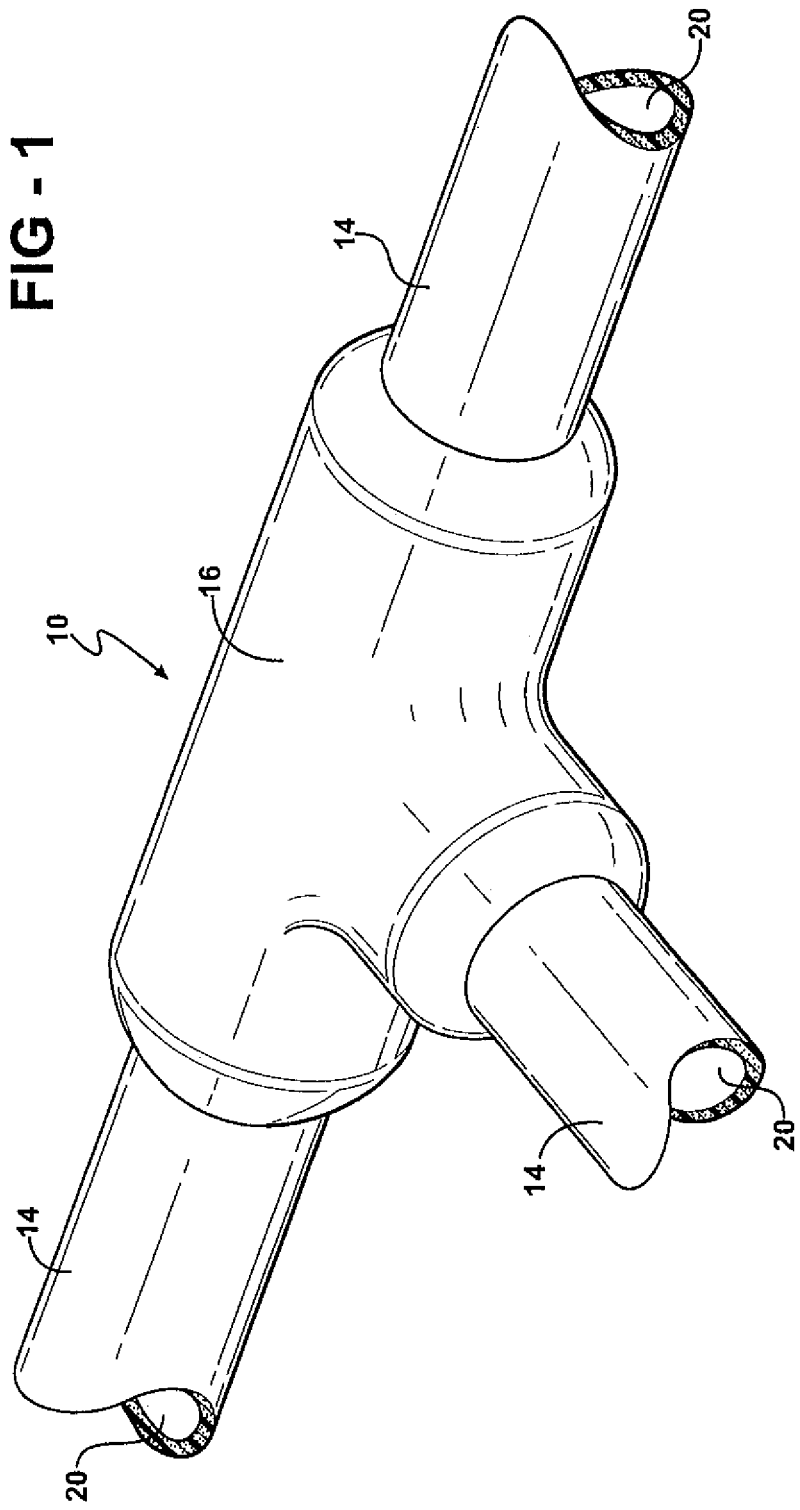

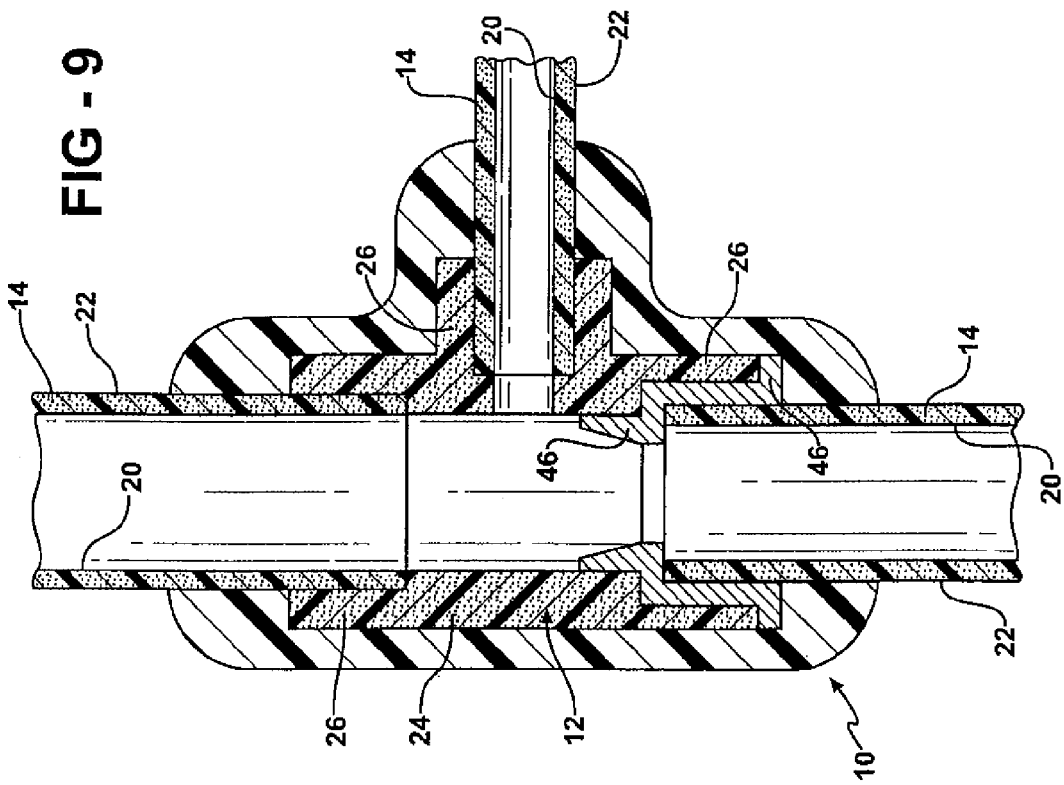
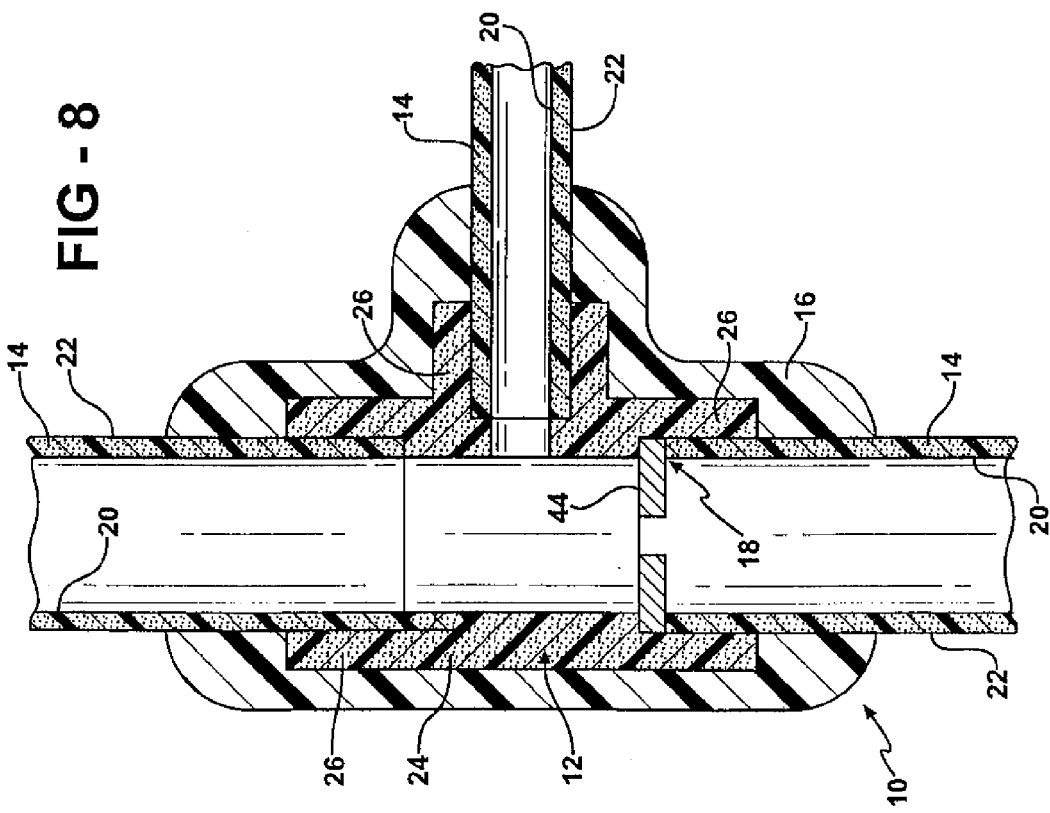

FLUID TRANSFER ASSEMBLY

RELATED APPLICATIONS

This application claims priority to and all the advantages of International Patent Application No. PCT/US2006/041573, filed on Oct. 23, 2006, which claims priority to United States Provisional Patent Application No. 60/729,427 filed on Oct. 21, 2005.

BACKGROUND OF THE INVENTION

1. Field of the Invention

The subject invention relates to a fluid transfer assembly for transferring liquids, such as medicinal substances, through a number of different tubes.

2. Description of Related Art

Fluid transfer assemblies having T-shaped or Y-shaped connectors for interconnecting three or more flexible tubes are well known in a variety of industries, such as the medical industry and the automotive industry. A typical T-shaped connector is illustrated in U.S. Pat. No. 6,308,992. The '992 patent discloses a T-shaped connector having a series of barbs with the tubes fitting over portions of the connector and interengaging the barbs to retain the tubes onto the T-shaped connector. Although the T-shaped connector of the '992 patent is specifically designed for an automotive application, similar T-shaped connectors are used in the medical industry.

Tubing used in the medical industry is frequently formed of silicone. Silicone is a relatively inert material such that the tubes and connector do not significantly degrade, react with or leach components as the medicinal substances pass through the tubes and connector. Other materials, such as polyvinyl chloride (PVC), are typically not used for transfer assemblies in pharmaceutical manufacturing as these materials can leach into the medicinal substances which will pollute the substance and destroy the purpose of the transfer assembly.

One drawback to the prior art connectors and tubes discussed above relates to a gap or void that is created between the tubes and the connector once the tubes are mounted to the connector. This gap or void can potentially accumulate medicinal substances which can then taint the proper dosage of the substance or be a location for potential microbiological growth. In addition, there is a potential that the tubes could become detached from the connector, which obviously creates a serious issue for appropriately transferring the medicinal substances.

One solution contemplated by the prior art eliminates the use of a traditional connector. As shown in U.S. Pat. No. 6,290,265, the connector and interconnection with the tubes are simultaneously created during a molding process. In particular, the tubes are inserted into a mold along with a rigid member. Liquid silicone is then injected into the mold about the tubes and the member. The liquid silicone is cured to form the connector and interconnect the tubes. Although the process for forming the transfer assembly shown in the '265 patent may avoid some of the issues described above, this process is considerably complicated and requires a number of steps to create the transfer assembly. Another solution contemplated by the prior art is shown in U.S. Pat. No. 6,432,345. The '345 patent discloses a T-shaped connector disposed within a mold and spaced from a plurality of tubes. Rigid pins interconnect the apertures of the connector with apertures of the tubes. Liquid silicone is then injected into the mold and is cured about the tubes and pins to interconnect the tubes to the manifold. The prior art system contemplated by the '345 patent may also avoid the deficiencies outlined above, but similarly suffers from being overly complicated and having numerous process steps.

Accordingly, there remains a need for developing a transfer assembly which is simple and easy to manufacture, minimizes voids or gaps which can accumulate substances, and securely fastens the tubes to the connector.

SUMMARY OF THE INVENTION AND ADVANTAGES

The subject invention includes a fluid transfer assembly comprising a plurality of flexible tubes formed of a first material composition comprising silicone. Each of the tubes has a free end and an inner bore. A manifold is formed of a second material composition, which also comprises silicone. The manifold has an inner protrusion and a plurality of connector portions. Each of the connector portions has an inner wall recessed from the inner protrusion and one complementary in configuration with corresponding free ends of the tubes. The free ends of the tubes are inserted within the complementary configured inner walls of the connector portions until each of the free ends abut the inner protrusion to create a continuous uninterrupted passageway between the inner bores of the tubes.

The subject invention also includes a method of assembling the flexible tubes in the manifold. The method comprises the steps of: inserting the free ends of the tubes within the complementary configured inner walls of the connector portion and abutting each of the free ends of the tubes with the inner protrusion of the manifold to create the continuous uninterrupted passageway between the inner bores of the tubes.

Accordingly, the subject invention sets forth a fluid transfer assembly with a manifold and tubes each being formed of silicone. The manifold has a particular advantageous structure which allows the tubes to be inserted within the connector portions of the manifold. Once assembled, an inner surface of the manifold aligns with an inner surface of the tubes such that any gaps or voids are minimized. The transfer assembly of the subject invention is therefore relatively simple to assemble and manufacture and avoids the pitfalls of the prior art systems discussed above.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a perspective view of a fluid transfer assembly in accordance with the subject invention;

FIG. 8 is a cross-sectional view of the manifold and tubes with an orifice plate disposed between the manifold and one of the tubes;

FIG. 9 is a cross-sectional view of the manifold and tubes with a reducer disposed between the manifold and one of the tubes;

DETAILED DESCRIPTION OF THE INVENTION

Figure 2:
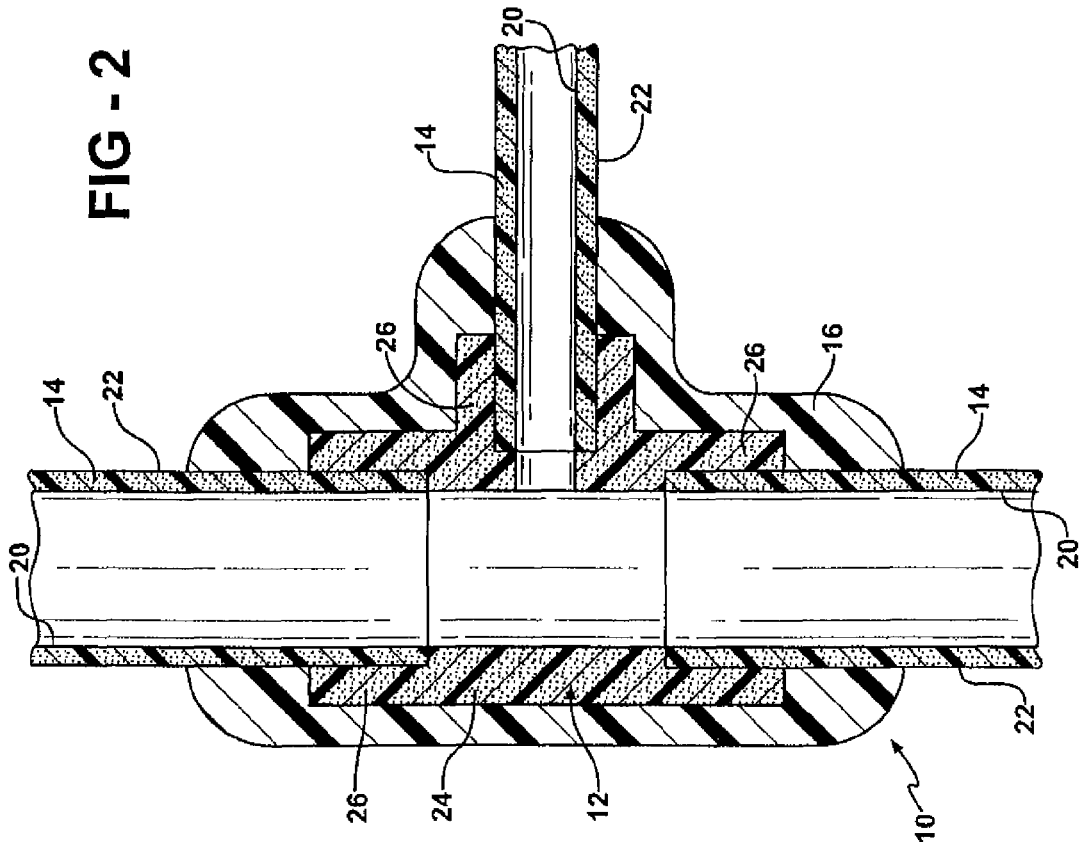
FIG. 2 is a cross-sectional view of the fluid transfer assembly of FIG. 1.

Referring to the Figures, wherein like numerals indicate like or corresponding parts throughout the several views, a fluid transfer assembly is generally shown at 10 in FIGS. 1 and 2. The fluid transfer assembly 10 includes a manifold 12 and a plurality of flexible tubes 14 inserted within the manifold 12. An outer capsule 16 is at least partially disposed over the manifold 12 and the tubes 14 after the tubes 14 are inserted within the manifold 12. The illustrative embodiment discloses the manifold 12 as substantially T-shaped having a single input and a pair of outputs. It should be appreciated that the manifold 12 may be of any suitable design or configuration, such as Y-shaped, and may include any number of inputs and any corresponding number of outputs. Similarly, the outer capsule 16 is disclosed as substantially T-shaped due to the T-shaped configuration of the manifold 12. It should also be appreciated that the outer capsule 16 may be of any suitable configuration.

The plurality of flexible tubes 14 are formed of a first material composition comprising silicone. Examples of suitable flexible tubes 14 include, but are not limited to, Dow Corning® Pharma Tubing, such as Dow Corning® Pharma-50, Dow Corning® Pharma Advanced Pump Tubing, and Dow Corning® Pharma-65 Reinforced Tubing, which are all commercially available from Dow Corning® of Midland, Mich. The manifold 12 is formed of a second material composition also comprising silicone. As discussed in the background section, silicone is a relatively inert material. Silicone is therefore used in this application such that the tubes 14 and manifold 12 will not significantly degrade, react with, leach or otherwise significantly absorb any medicinal substances as the medicinal substances pass through the tubes 14 and manifold 12. It is preferred that the first and second material compositions contain no peroxide by-products, chlorophenyls, or PCBs. Further, the first and second material compositions preferably do not include any organic plasticizers, phthalates, or latex additives.

In one embodiment, the first and second material compositions are the same. Preferably, the first and second material compositions are further defined as silicone rubber, such as polydimethylsiloxane (PDMS) based silicone rubber. Further the silicone rubber could be a high consistency silicone rubber (HCR) or liquid silicone rubber (LSR). HCRs are also generally referred to throughout the art as high consistency elastomers (HCEs). It should be appreciated that the first and second material compositions must be suitably qualified for pharmaceutical applications. If desired, the silicone material could be mixed with polymeric materials including, but not limited to, polyurethanes, acrylics, esters, or other thermoplastic elastomers (TPEs). These polymeric materials should be substantially impervious, non-reactive, and non-additive to medicinal substances passing therethrough, which would prevent degradation of the tubes 14 or the manifold 12. Preferably, the first and second material compositions comprising the alternative polymeric material would include at least 10% silicone by weight of each of the tubes 14 or the manifold 12. As discussed above, silicone is a relatively inert material such that the inclusion of the silicone into the polymeric material would reduce the likelihood of degradation of the tubes 14 or manifold 12, reducing the likelihood of product contamination.

Although the first and second material compositions of the tubes 14 and manifold 12, respectively, may be the same and may even be the same HCR, the manifold 12 is generally substantially non-pliable as compared to the flexible tubes 14 due to its larger body. In addition, each of the tubes 14 and the manifold 12 may have a similarly and preferably common Shore A hardness, generally ranging from 35-80, more preferably from 50-80. However, even with a common Shore A hardness, the manifold 12 is substantially non-pliable as compared to the flexible tubes 14. In other words, the manifold 12 is substantially rigid as compared to the flexible tubes 14. This difference in rigidity between the manifold 12 and the flexible tubes 14 is due to the unique structural configuration of the manifold 12 as is discussed in greater detail below.

Alternatively, the first and second material compositions could be different, so long as silicone is present. In particular, the first material composition of each of the tubes 14 or the second material composition of the manifold 12 could be further defined as silicone rubber, such as an HCR or LSR. In other words, one of the manifold 12 or the tubes 14 could be formed of an alternative suitable material other than HCR or LSR. Similarly, the first material composition of each of the tubes 14 or the second material composition of the manifold 12 could be defined as the PDMS based silicone rubber such that the other of the manifold 12 or the tubes 14 could be formed of an alternative suitable material. Other suitable materials can include the alternative polymeric materials discussed above.

Figures 3, 4:
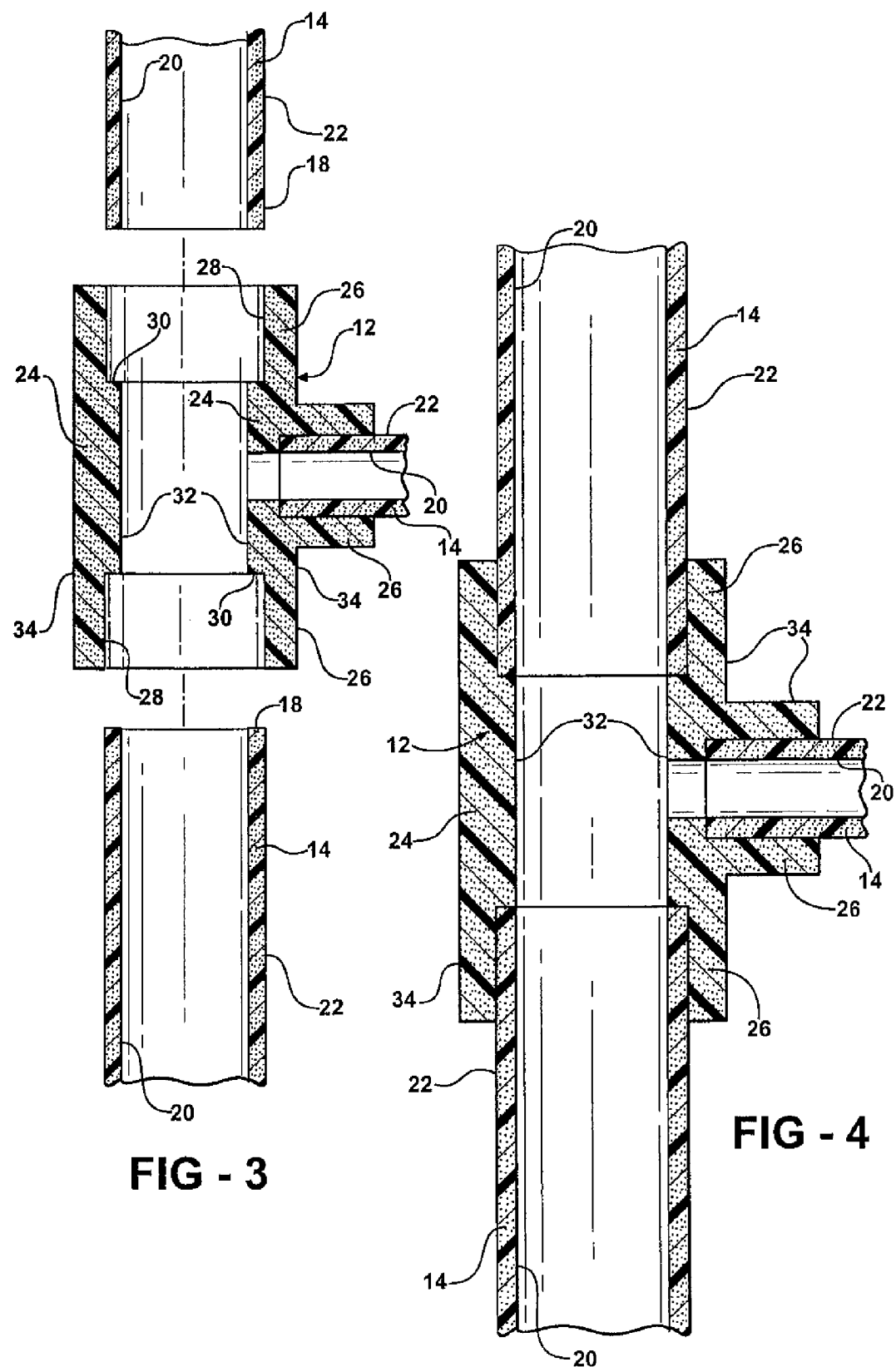
FIG. 3 is a cross-sectional view of a manifold with a pair of tubes in spaced relationship thereto.
FIG. 4 is a cross-sectional view of the manifold with all of the tubes connected to the manifold.

Referring also to FIGS. 3 and 4, the structural attributes of the manifold 12 and tubes 14 will now be discussed in greater detail. In particular, each of the tubes 14 have a free end 18 and an inner bore 20. The tubes 14 also have an exterior surface 22 with the bores 20 having an interior surface. The distance between the exterior surface 22 and the interior surface 20 of each tube 14 defines a thickness of each tube 14. Each of the tubes 14 has a modulus of elasticity and elongation characteristics that create a substantially flexible tube 14. For example, tubes 14 formed from Dow Corning® Pharma Tubing typically has a modulus of elasticity at 200% elongation ranging from 2.1 MPa (at Shore A hardness of 50) to 3.9 MPa (at Shore A hardness of 80). The typical percent elongation at a break point of tubes 14 formed from Dow Corning® Pharma Tubing ranges from 795% (at Shore A hardness of 50) to 570% (at Shore A hardness of 80).

The manifold 12 has an inner protrusion 24 and a plurality of connector portions 26. Each of the connector portions 26 have an inner wall 28 recessed from the inner protrusion 24. Each of the connector portions 26 are complementary in configuration with corresponding free ends 18 of one of the tubes 14. In other words, inner walls 28 of the connector portions 26 are of a configuration that is generally similar to a configuration of the exterior surface 22 of a corresponding tube 14 such that the tubes 14 can be adequately disposed within the connector portions 26. It should be appreciated that the configuration of the inner walls 28 of the connector portions 26 are not necessarily identical to the configuration of the exterior surface 22 of the corresponding tube 14. In fact, the alternative embodiments set forth below illustrate examples of the connector portions 26 being complementary in configuration to the tubes 14 yet not being identical. Referring to FIG. 3, the input of the manifold 12 defines a connector portion 26 that is smaller in diameter than the connector portions 26 defined by the outputs of the manifold 12. It should be appreciated that this particular configuration of inputs and outputs is in no way limiting to the subject invention. Preferably, the connector portions 26 of the manifold 12 will be sized appropriately depending upon the inner and outer diameters of the tubes 14.

The method of assembling the flexible tubes 14 and manifold 12 includes the step of inserting the free ends 18 of the tubes 14 within the complementary configured inner walls of the connector portions 26. This insertion continues until each of the free ends 18 of the tubes 14 abuts the inner protrusion 24 of the manifold 12 to create a continuous uninterrupted passageway between the inner bores 20 of the tubes 14 (See FIGS. 2 and 4). The free ends 18 of the tubes 14 can be prepared for improved adhesion within the connection portions 26. For example, the free ends 18 of the tubes 14 could include a matted or roughen finish by means such as sanding, plasma or corona treatment, or mirco-abrasion. Further, the free ends 18 could be prepared using a primer. The same preparations could be performed on the inner surface 28 of manifold 12.

As best shown in FIG. 3, the inner protrusion 24 defines a plurality of abutment surfaces 30. It should be appreciated that the inner protrusion 24 can define any number of abutment surfaces 30 which will primarily depend upon the number of tubes 14 that are being inserted into the manifold 12. The abutment surfaces 30 have a predetermined height which is substantially equal to the thickness of the tubes 14, i.e. the walls, to define the smooth uninterrupted passageway when the tubes 14 are inserted into the manifold 12. In one preferred embodiment, the inner protrusion 24 is a continuous inner band within the manifold 12 that defines a inner surface 32. An aperture is disposed through the inner protrusion 24 to fluidly connect one of the connector portions 26 to the remaining connector portions 26.

The manifold 12 is preferably formed of a homogeneous material such that the connector portions 26 and the inner protrusion 24 are preferably formed together. The manifold 12 also has an exterior surface 34 with a distance between the exterior surface 34 of the manifold 12 and the inner wall 28 defining a first thickness of the manifold 12. Also, a distance between the exterior surface 34 of the manifold 12 and the inner surface 32 of the inner protrusion 24 defines a second thickness of the manifold 12. Preferably, the second thickness is greater than the first thickness of the manifold 12. Even more preferably, the first and second thicknesses of the manifold 12 are greater than the thicknesses of the tubes 14 such that the manifold 12 is substantially non-pliable, i.e. rigid, as compared to the flexible tubes 14. As mentioned above, the manifold 12 and flexible tubes 14 are preferably formed of a similar or same material. As such, the manifold 12 is non-pliable or rigid due to the unique configuration and increased thickness of the manifold 12 as viewed in cross-section.

Turning back to the method of assembling the flexible tubes 14 and the manifold 12, an adhesive may be applied between the connector portions 26 and the tubes 14 before the free ends 18 of the tubes 14 are inserted into the connector portions 26. The adhesive would preferably comprise silicone and would be utilized to further secure the tubes 14 within the manifold 12 in addition or in lieu of the outer capsule 16 discussed above and discussed in greater detail below. The adhesive would be disposed between the tubes 14 and the inner walls 28 to further secure the tubes 14 within the manifold 12 in a similar manner as the lubricant 54 shown in FIG. 12. It should be appreciated that the adhesive could be any suitable material that behaves like an adhesive.

Figure 5:
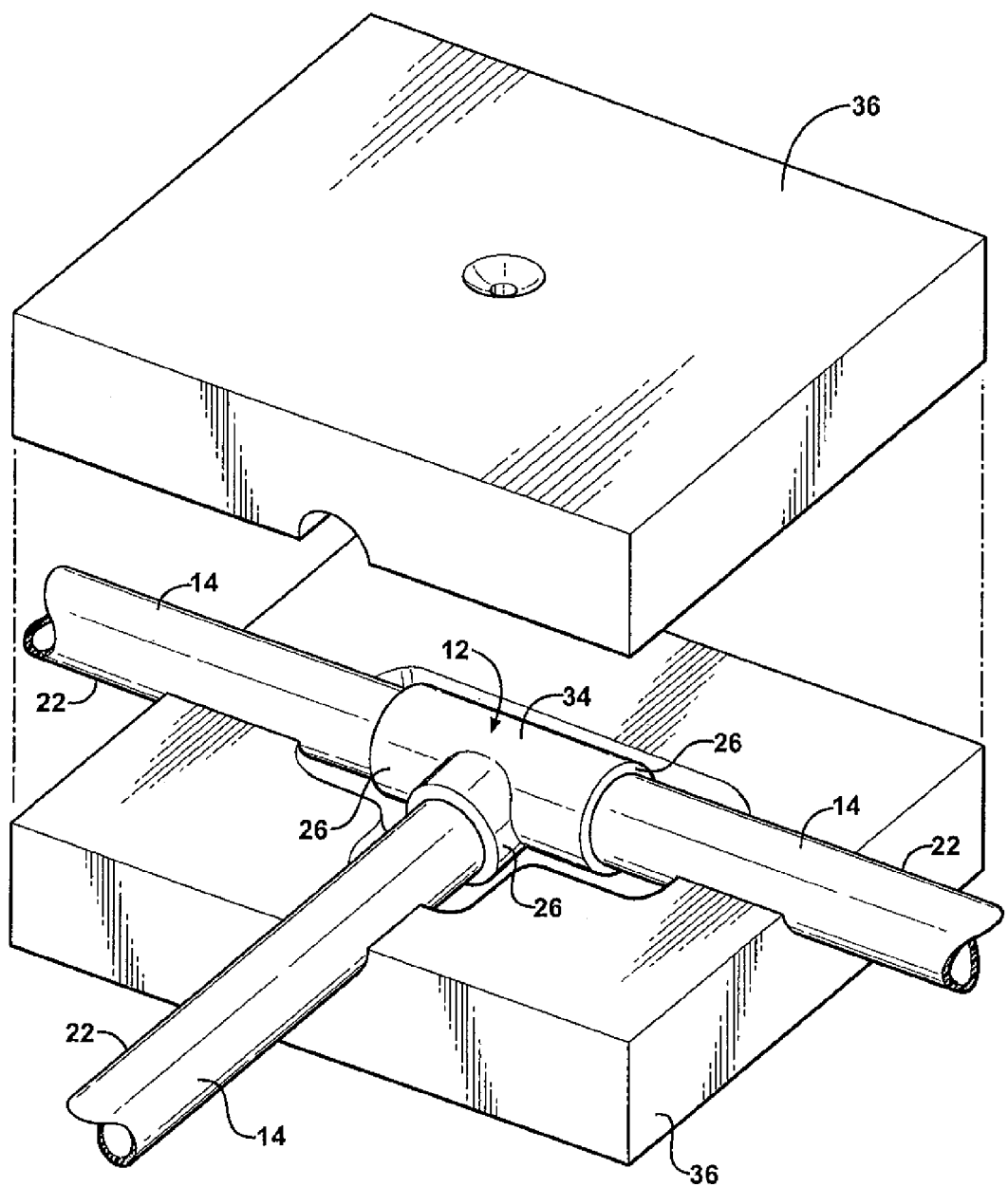
FIG. 5 is a perspective view of the fluid transfer assembly disposed within a molding assembly.

As shown with FIG. 5, the assembled manifold 12 and tubes 14 are optionally placed into a molding assembly 36. The molding assembly 36 is shown schematically and could be of any suitable design or configuration. The adhesive may be used as a means to retain the tubes 14 within the manifold 12 during this molding operation. Alternatively, the free ends 18 of the tubes 14 could be soaked in a solvent such that the free ends 18 will swell, which in turn assists in retaining the tubes 14 in the manifold 12 during the molding operation. Silicone rubber is introduced into the molding assembly 36 about the manifold 12 and tubes 14. Preferably, high consistency or liquid silicone rubber is injected into the molding assembly 36. The silicone is then cured to define the outer capsule 16 and to secure the tubes 14 to the manifold 12. It should be appreciated that the outer capsule 16 could be formed at any other silicone containing material, such as Dow Corning® Silicone Foam or Dow Corning® Polyurethane Potting Compounds. The foams could be used with or without a mold.

Referring back to FIGS. 1 and 2, the outer capsule 16 is preferably molded over at least a portion of the manifold 12 and the tubes 14 after the free ends 18 of the tubes 14 abut the inner protrusion 24. Even more preferably, the outer capsule 16 is molded over the entire exterior surface 34 of the manifold 12 to completely encapsulate the manifold 12. The exterior surface of manifold 12 can be prepared for improved adhesion of the over mold outer capsule 16. The exterior surface 34 of manifold 12 could include a matted or roughened finish by means such as sanding, plasma or corona treatment or micro abrasion. Further, the exterior surface could be prepared using a primer. Simultaneously, the outer capsule 16 is molded over a portion of the exterior surface 22 of each of the tubes 14 to encapsulate this portion of each of the tubes 14. During the molding of the outer capsule 16, gas may be injected into the tubes 14 to prevent the tubes 14 from collapsing. Alternatively, securing devices, such as hose clamps (not shown), may be used on the exterior surface 34 of the manifold 12 in lieu of molding to secure the tubes 14 to the manifold 12. As an additional alternative, the outer capsule 16 could be formed using a heat shrink material comprising silicone for securing the tubes 14 to the manifold 12.

Figure 6:
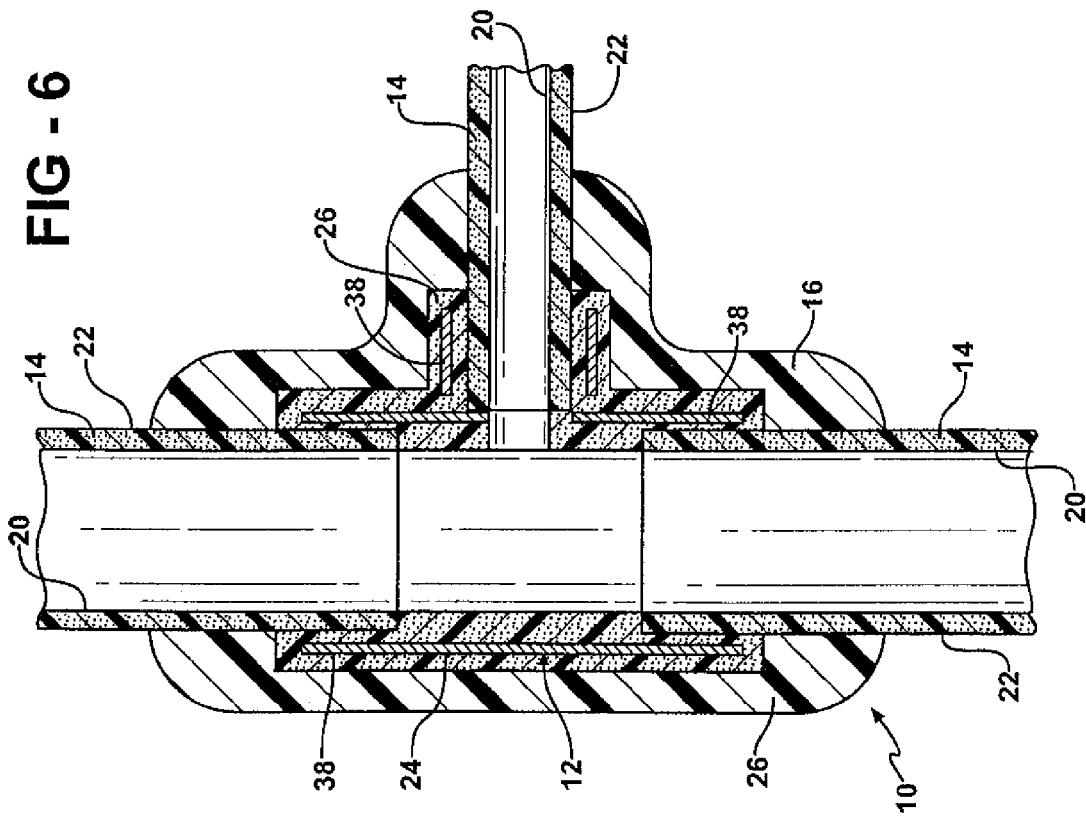
FIG. 6 is a cross-sectional view of an alternative manifold having reinforcement elements disposed therein.

Turning to FIGS. 6-14, various alternative embodiments of the manifold 12 and tubes 14 are shown, wherein like numerals indicate like or corresponding parts. As shown in FIG. 6, at least one reinforcement element 38 is integrally formed within the manifold 12 for providing additional rigidity to the manifold 12. As illustrated, there is a pair of tubular reinforcement elements 38 disposed in opposing directions. The reinforcement elements 38 can be formed of a rigid metallic or polymeric material and are preferably encased within the manifold 12.

Figure 7:
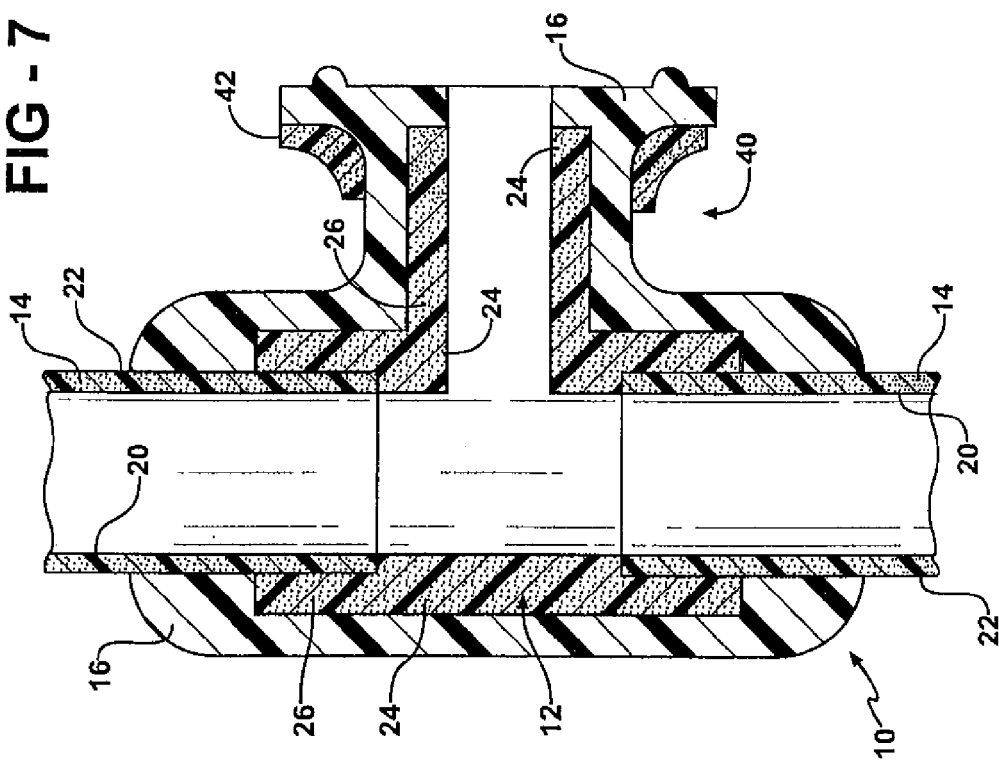
FIG. 7 is a cross-sectional view of another alternative manifold forming a clamp connection once an outer capsule is molded about the manifold.

Turning to FIG. 7, a clamp connection 40 is integrally formed by an alternative manifold 12 and the outer capsule 16 at one end of the manifold 12. The clamp connection 40 provides an integrally molded sanitary mounting point for the manifold 12. The manifold 12 of this embodiment eliminates one of the inner walls 28 of the connector portions 26 and, in essence, extends the inner protrusion 24 to the end of the connector portion 26. The connector portion 26 is then entirely encased with the outer capsule 16. The outer capsule 16 can also include an annular filet 42 for providing a mounted point for the clamp connection 40 and the manifold 12.

Figure 10:
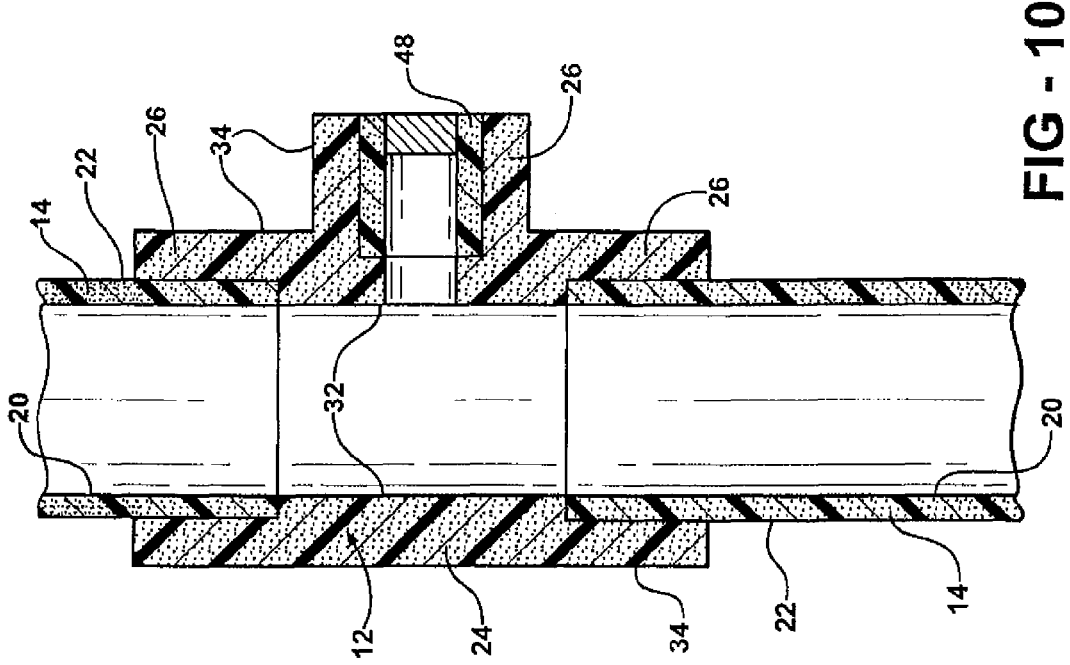
FIG. 10 is a cross-sectional view of the manifold and tubes with a septum element disposed within the manifold.

As shown in FIG. 8, an orifice plate 44 can be disposed between the free end 18 of one of the tubes 14 and the inner protrusion 24 for reducing or restricting a flow of material through the corresponding tube 14. Also, as shown in FIG. 9, a reducer 46 may be disposed within one of the inner walls 28 of the manifold 12 for accepting tubes 14 having an outer diameter smaller than an inner diameter of the corresponding inner wall 28. In other words, the use of the reducer 46 allows for smaller sized tubes 14 to be installed on the same manifold 12 without modifying the manifold 12 itself. Preferably, the reducer 46 is inserted into the connector portion 26 of the manifold 12 before the smaller sized tube 14 is inserted. As shown in FIG. 10, a septum element 48 could be disposed within one of the inner walls 28 of the manifold 12. The septum element 48 includes a plug of soft material which prevents leakage of material yet allows for insertion of a needle, such as a hypodermic needle (not shown).

Figure 11:
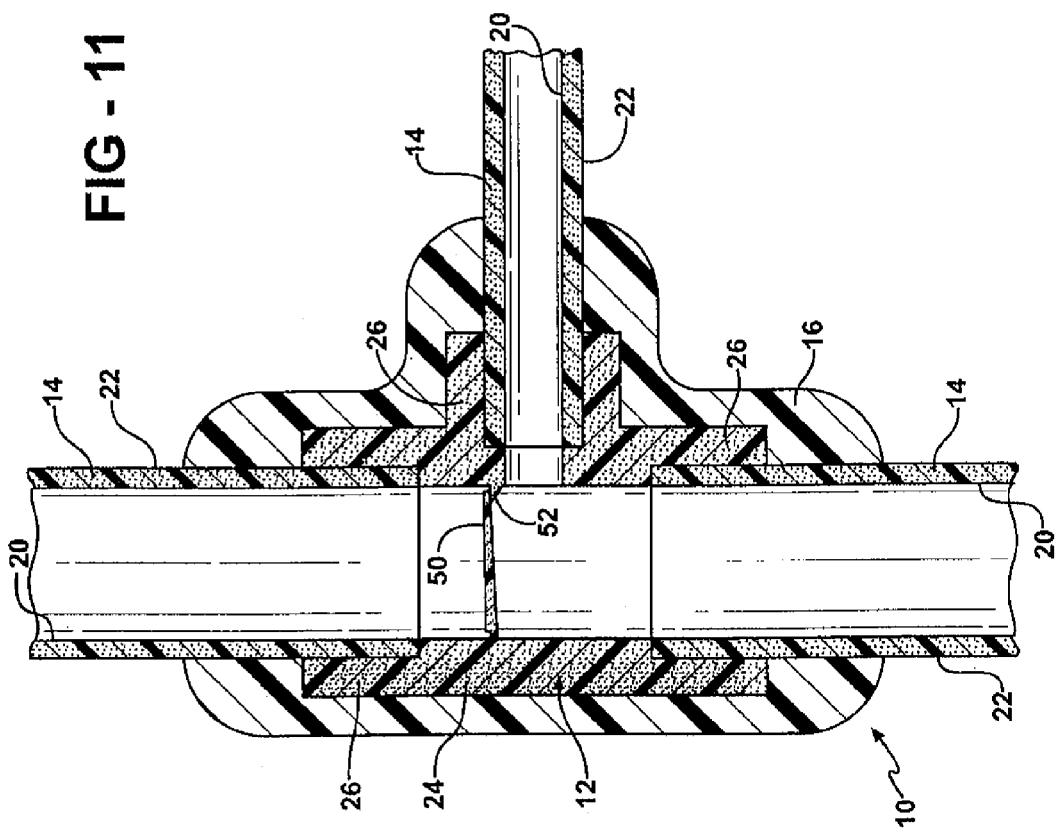
FIG. 11 is a cross-sectional view of yet another alternative manifold having a valve disposed therein.

Turning to FIG. 11, another alternative manifold 12 is shown, which includes a valve 50 disposed within the inner protrusion 24 of the manifold 12. The valve 50 is designed as a one-way valve 50 allowing a flow of material in one direction but restricting a flow of the material in an opposing direction. The valve 50 is illustrated as a flap 50 having a living hinge interconnecting the flap 50 to the manifold 12. A stop 52 extends from an opposing side of the inner protrusion 24 to restrict the pivotal movement of the flap 50.

Figure 12:
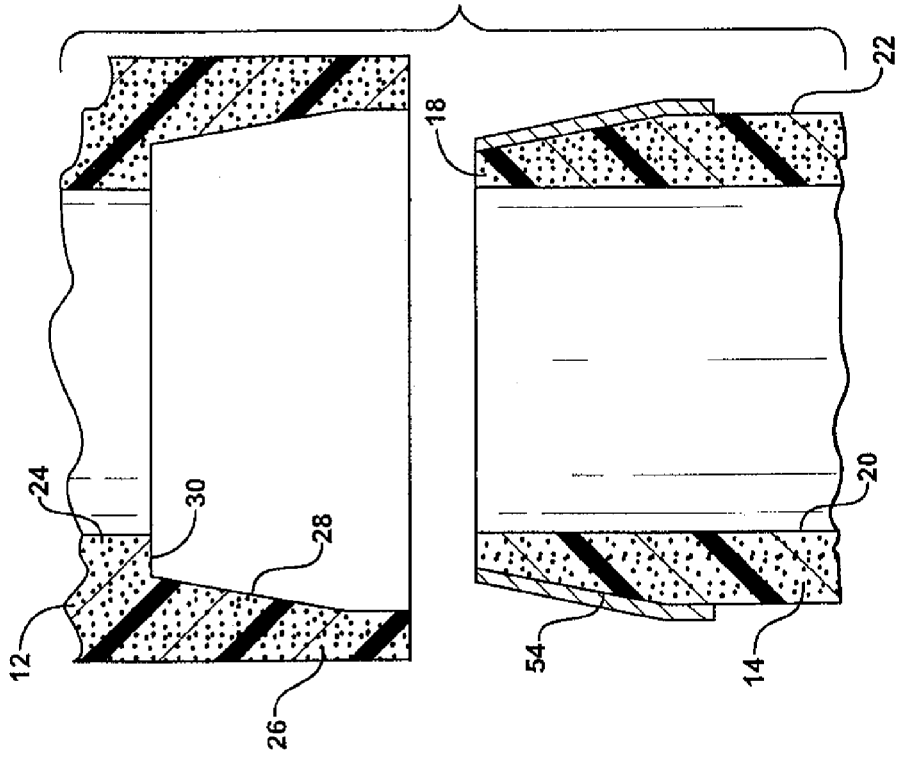
FIG. 12 is a fragmented cross-sectional view of an alternative manifold and an alternative tube with the manifold and tube having tapered ends.
Figure 14:
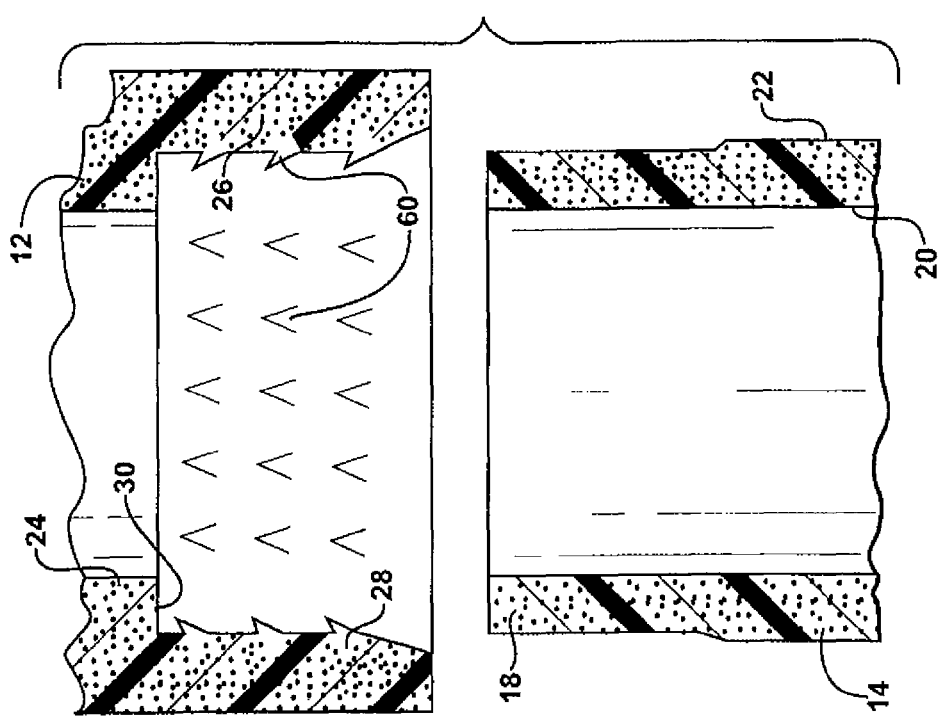
FIG. 14 is a fragmented cross-sectional view of yet another alternative manifold and yet another alternative tube with the manifold having barbs.
Figure 13:
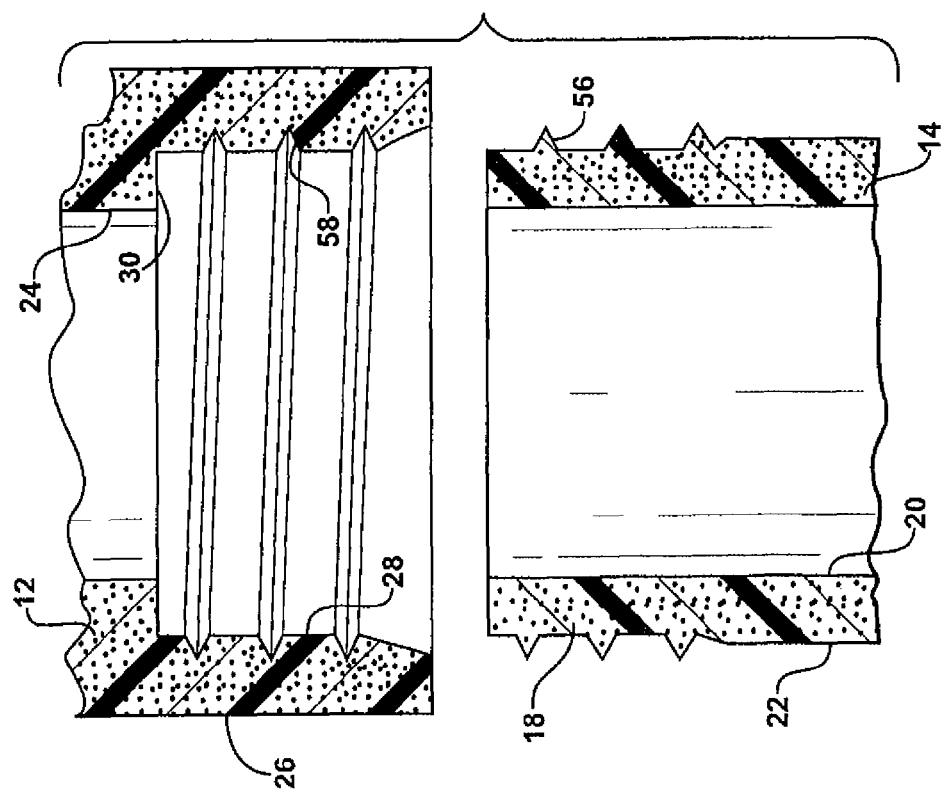
FIG. 13 is a fragmented cross-sectional view of another alternative manifold and another alternative tube with the manifold and tube having a set of threads.
Figure 15:
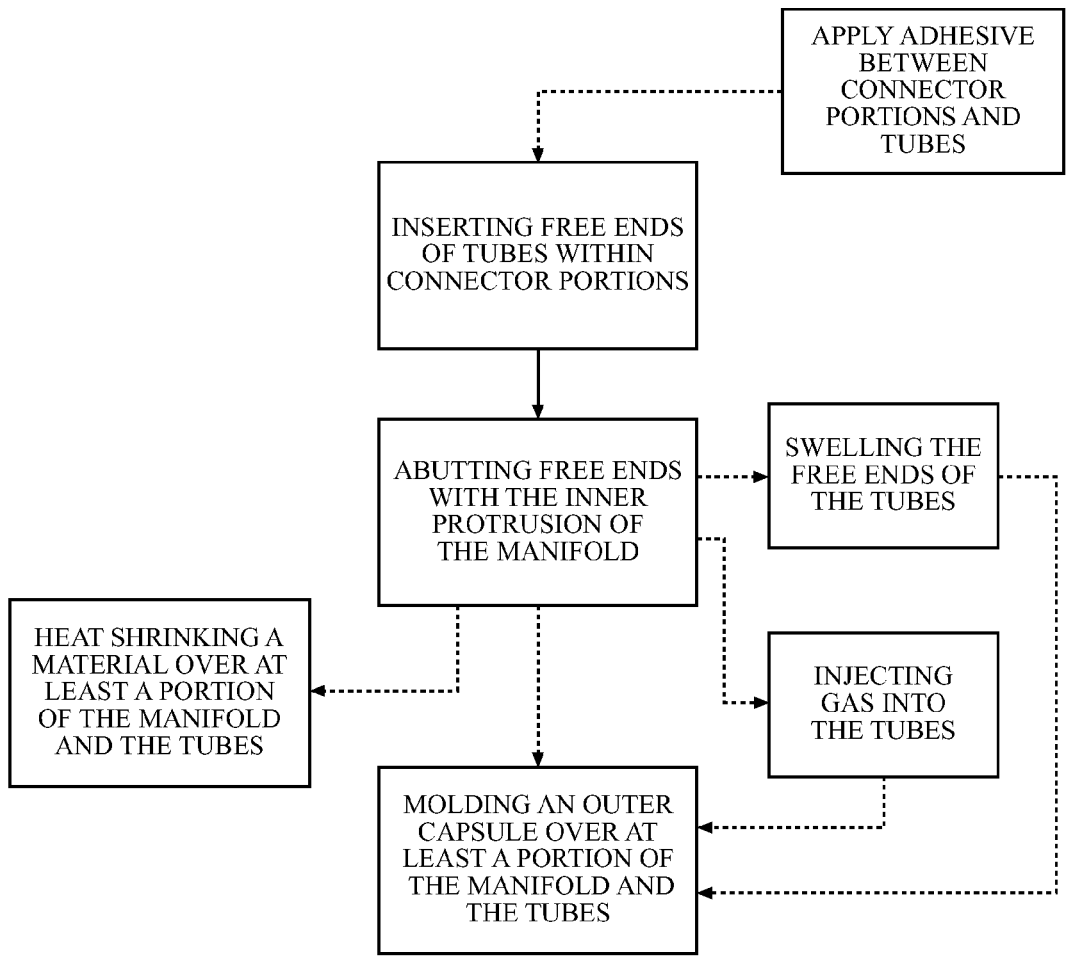
FIG. 15 is a flow chart illustrating various steps of the subject invention.

FIGS. 12-14 illustrate various alternative designs of one of the tubes 14 and a portion of the manifold 12. In particular, FIG. 12 shows that at least one of the free ends 18 of the tubes 14 can be tapered and the corresponding inner wall 28 of the manifold 12 would also be tapered for receiving the tapered free end 18 of the tubes 14. The tapered tube 14 and manifold 12 would allow for easier insertion of the tube 14 into the manifold. Further, a lubricant 54 may be disposed between the exterior surface 22 of the free end 18 and the inner wall 28 for assisting the insertion of the tubes 14 into the manifold 12. The lubricant 54 is shown schematically in FIG. 12. The lubricant 54 could be a solvent, such as isopropyl alcohol, or a silicone based material such as PDMS.

As shown in FIG. 13, at least one of the free ends 18 of the tubes 14 could alternatively include a first set of threads 56 and at least one the inner walls 28 of the manifold 12 could alternatively include a corresponding second set of threads 58 for receiving the first set of threads 56 on the tubes 14. The adhesive discussed above could be used in this threading application. Alternatively, as shown in FIG. 14, barbs 60 could be disposed on at least one of the free ends 18 and the inner walls 28 for securing the tubes 14 within the manifold 12 after the tubes 14 are inserted into the manifold 12. As illustrated, a plurality of barbs 60 are spaced about the inner wall 28 of one of the connector portions 26 of the manifold 12.

As should be readily apparent from the above description, the subject invention incorporates a manifold 12, which could have various alternative features, of a simplified construction and an assembly process for inserting the tubes 14 into the manifold 12 which is of a simple and eloquent design. The assembled transfer assembly 10 avoids the pitfalls of creating any significant gaps or voids within the manifold 12 itself. The over molding of the outer capsule 16 provides a secure and virtually permanent inner-connection of the tubes 14 to the manifold 12.

The invention has been described in an illustrative manner, and it is to be understood that the terminology which has been used is intended to be in the nature of words of description rather than of limitation. As is now apparent to those skilled in the art, many modifications and variations of the present invention are possible in light of the above teachings. It is, therefore, to be understood that within the scope of the appended claims the invention may be practiced otherwise than as specifically described.

What is claimed is:

1. A fluid transfer assembly comprising:
    a plurality of flexible tubes formed of a first material composition comprising silicone with each of said tubes having a free end and an inner bore defining a cavity;
    a manifold formed of a second material composition comprising silicone and having an inner protrusion and a plurality of connector portions with said inner protrusion defining an aperture fluidly connecting said connector portions and each of said connector portions having an inner wall recessed from said inner protrusion and complementary in configuration with corresponding free ends of said tubes whereby said free ends of said tubes are inserted within said complementary configured inner walls of said connector portions until each of said free ends abut said inner protrusion to fluidly connect said cavities of said flexible tubes with said aperture of said inner protrusion to create a continuous uninterrupted passageway between said cavities of said inner bores of said tubes; and
    an outer capsule at least partially disposed over said manifold and said tubes after said tubes are inserted within said manifold.

2. An assembly as set forth in claim 1 wherein said first and second material compositions are the same.

3. An assembly as set forth in claim 2 wherein said manifold is substantially non-pliable as compared to said flexible tubes.

4. An assembly as set forth in claim 1 wherein said first and second material compositions are further defined as silicone rubber.

5. An assembly as set forth in claim 1 wherein each of said tubes and said manifold have a similar Shore A hardness and said manifold is substantially non-pliable as compared to said flexible tubes.

6. An assembly as set forth in claim 1 wherein said second material composition is further defined as silicone rubber.

7. An assembly as set forth in claim 1 wherein said second material composition comprises at least 10 percent silicone by weight of said manifold.

8. An assembly as set forth in claim 1 wherein;
    each of said tubes have an exterior surface and said bores have an interior surface defining said cavities with a distance between said exterior surface and interior surfaces defining a thickness of said tubes,
    said inner protrusion defines a plurality of abutment surfaces, and
    said abutment surfaces have a height substantially equal to said thickness of said tubes to define said uninterrupted passageway.

9. An assembly as set forth in claim 8 wherein;
    said manifold has an exterior surface with a distance between said exterior surface of said manifold and said inner wall defining a first thickness of said manifold, said inner protrusion includes an inner surface defining said aperture with a distance between said exterior surface of said manifold and said inner surface of said inner protrusion defining a second thickness of said manifold which is greater than said first thickness of said manifold, and each of said first and second thicknesses of said manifold are greater than said thicknesses of said tubes such that said manifold is substantially non-pliable as compared to said flexible tubes.

10. An assembly as set forth in claim 1 wherein said tubes and said manifold each have an exterior surface with said outer capsule completely encapsulating said exterior surface of said manifold and encapsulating a portion of each of said exterior surfaces of said tubes.

11. An assembly as set forth in claim 10 further including at least one clamp connection integrally formed by said manifold and said outer capsule for providing a mounting point for said manifold.

12. An assembly as set forth in claim 1 wherein said outer capsule is formed from silicone rubber.

13. An assembly as set forth in claim 1 further including an adhesive comprising silicone with said adhesive disposed between said tubes and said inner walls to further secure said tubes within said manifold.

14. An assembly as set forth in claim 1 further including a lubricant disposed between said free ends and said inner walls for assisting said insertion of said tubes into said manifold.

15. An assembly as set forth in claim 1 further including barbs disposed on at least one of said free ends and said inner walls for securing said tubes within said manifold after said tubes are inserted into said manifold.

16. An assembly as set forth in claim 1 wherein at least one of said free ends of said tubes is tapered and at least one of said inner walls of said manifold is tapered for receiving said tapered free end of said tube.

17. An assembly as set forth in claim 1 wherein at least one of said free ends of said tubes includes a first set of threads and at least one of said inner walls of said manifold includes a second set of threads for receiving said first set of threads on said tube.

18. An assembly as set forth in claim 1 further including at least one reinforcement element integrally formed within said manifold for providing additional rigidity to said manifold.

19. A method of assembling a plurality of flexible tubes and a manifold each comprising silicone with each of the tubes having a free end and an inner bore defining a cavity and the manifold having an inner protrusion and a plurality of connector portions with the inner protrusion defining an aperture fluidly connecting the connector portions and each of the connector portions having an inner wall recessed from the inner protrusion, said method comprising the steps of:

inserting the free ends of the tubes within complementary configured inner walls of the connector portions; and abutting each of the free ends of the tubes with the inner protrusion of the manifold to fluidly connect the cavities of the flexible tubes with the aperture of the inner protrusion to create a continuous uninterrupted passageway between the cavities of the inner bores of the tubes.

20. A method as set forth in claim 19 further including the step of molding an outer capsule over at least a portion of the manifold and the tubes after the step of abutting the free ends of the tubes with the inner protrusion.

21. A method as set forth in claim 20 wherein the step of molding an outer capsule is further defined as molding the outer capsule over an entire exterior surface of the manifold to completely encapsulate the manifold and simultaneously molding the outer capsule over a portion of an exterior surface of each of the tubes to encapsulate the portion of each of the tubes.

22. A method as set forth in claim 20 wherein the step of molding an outer capsule includes the step of introducing silicone about the manifold and tubes after the step of abutting the free ends of the tubes with the inner protrusion.

23. A method as set forth in claim 22 wherein the step of molding the outer capsule includes the step of curing the silicone to define the outer capsule and to secure the tubes to the manifold.

24. A method as set forth in claim 20 further including the step of injecting gas into the tubes during the step of molding the outer capsule to prevent the tubes from collapsing.

25. A method as set forth in claim 20 further including the step of swelling the free ends of the tubes disposed within the manifold for retaining the tubes in the manifold during the step of molding the outer capsule.

26. A method as set forth in claim 19 further including the step of applying an adhesive between the connector portions and the tubes before the free ends of the tubes are inserted into the connector portions.

27. A method as set forth in claim 19 further including the step of heat shrinking a material over at least a portion of the manifold and the tubes after the step of abutting the free ends of the tubes with the inner protrusion.

* * * * *

UNITED STATES PATENT AND TRADEMARK OFFICE
CERTIFICATE OF CORRECTION

| | | |
|---|---|---|
| PATENT NO. | : 8,424,923 B2 | Page 1 of 1 |
| APPLICATION NO. | : 12/090815 | |
| DATED | : April 23, 2013 | |
| INVENTOR(S) | : William D. Inman, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this
Sixteenth Day of December, 2014

Michelle K. Lee
*Deputy Director of the United States Patent and Trademark Office*